United States Patent [19]
Nacson

[11] Patent Number: 5,395,589
[45] Date of Patent: Mar. 7, 1995

[54] APPARATUS FOR RAPID AND SPECIFIC DETECTION OF ORGANIC VAPORS

[75] Inventor: Sabatino Nacson, Willowdale, Canada

[73] Assignee: Scintrex Limited, Concord, Canada

[21] Appl. No.: 224,143

[22] Filed: Apr. 7, 1994

[30] Foreign Application Priority Data

Apr. 6, 1994 [CA] Canada .................................. 2120682

[51] Int. Cl.⁶ ............................................. G01N 30/00
[52] U.S. Cl. ....................................... 422/88; 422/52;
422/83; 422/90; 422/98; 55/270; 73/35;
73/23.2; 73/31.01; 95/97; 95/50; 96/154;
423/DIG. 39; 436/106; 436/118; 436/155
[58] Field of Search ....................... 422/52, 83, 88, 90,
422/98; 436/106, 116–118, 155, 149, 172;
73/35, 23.2, 31.01; 55/270, 274; 96/154, 146,
111; 95/47, 50, 148; 423/DIG. 39

[56] References Cited

U.S. PATENT DOCUMENTS 5,308,481 5/1994 Stalling et al. ................... 210/198.2

OTHER PUBLICATIONS

Cohen et al., "Rotational and State–Resolved Translational Distributions of NO Scattered from Organized Amphiphilic Monolayers", J. Chem. Phys., vol. 88, No. 4, pp. 2757–2763 (1988).
Paz et al., "Vibrational Population Inversion in Aniline following Trapping/Desorption from Fullerene Surfaces", J. Phys. Chem., vol. 96, No. 8, pp. 3186–3188 (1992).
Abraham et al., "Fullerene as an Adsorbent for Gases and Vapours", J. Chem. Soc. Chem. Commun., vol. 24, pp. 1863–1864 (1993).
Abraham et al., "A New Method for the Characterization of the Adsorption of Gases and Vapours on Solids", J. Chromatography, vol. 409, pp. 15–27 (1987).
D. P. Lucepo, Anal. Chemistry, 40, 707, 1968.
S. Nacson, et al., Canadian Conference on Electrical and Computer Engineering, Canada, 1990.
G. P. Cobb, et al., Proceedings of the 1986, EPA-/APCA Symp. Measurement of Toxic Air Pollutants, pp. 314–319.
A. L. Lafleur, et al., Anal. Chemistry, 1981, 53, p. 1202.
M. Krzymien, et al., Scientific Inst., vol. 9, pp. 584–586, 1976.

Primary Examiner—James C. Housel
Assistant Examiner—Jan M. Ludlow
Attorney, Agent, or Firm—Sim & McBurney

[57] ABSTRACT

Apparatus for preconcentrating trace amounts of organic vapors in a sample of air for subsequent detection, comprising a metallic substrate; a thin film of fullerenes deposited on the metallic substrate for adsorbing the organic vapors on the thin film of fullerenes, thereby preconcentrating the organic vapors; and apparatus for heating the metallic substrate to a predetermined optimum temperature for desorbing the vapors from the thin film of fullerenes to form desorbed organic vapors for subsequent detection.

12 Claims, 3 Drawing Sheets

APPARATUS FOR RAPID AND SPECIFIC DETECTION OF ORGANIC VAPORS

FIELD OF THE INVENTION

This invention relates in general to illicit drug and explosive detection equipment, and more particularly to a novel preconcentrator which utilizes fullerenes as the adsorber material for collecting target organic vapours with high collection efficiency and with a high degree of specificity, and releasing the target vapours in a short time period for subsequent detection.

BACKGROUND OF THE INVENTION

There are many applications for the detection of trace amounts of specific organic substances, which require a combination of high sensitivity, high specificity and a short time of measurement. Included in these applications are the detection of illicit drugs, concealed explosives and chemical agents, etc. For some applications it is advantageous to simultaneously detect the presence of one or more of a common family of vapours, (e.g. of organonitrate explosives, or of illicit drugs, etc).

Some of the substances referred to above have a sufficiently high vapour pressure to produce detectible levels of their vapours at room temperature (e.g. EGDN and TNT, etc.). Other substances have very low volatility (e.g. cocaine, heroin and plastic explosives) and must be gathered in the form of particulates, and then heated to produce vapours for detection and analysis.

Ultimately, however, all detection devices for these applications operate on a vapour phase detection basis wherein the required threshold sensitivity of detection is commonly in the parts-per-billion, or even part-per-trillion level, in the original sample of air. Since the ultimate detector for the target organic vapours may not have sufficiently high intrinsic sensitivity, it is common practice to use a preconcentrator device. This device serves to raise the level of the target vapours by collecting them over a period of time, from a relatively large volume of air, and then releasing them into a much smaller volume of air or carrier gas for detection.

Essential characteristics of a preconcentrator for specific target vapours are a high efficiency in the collection of these vapours from the incoming volume of air, and a high degree of specificity, (i.e. preference for the collection of the target vapours), in the presence of a large quantity of extraneous substances in the original sample volume. In addition, where a short time of measurement is essential for a specific application, the time of release (desorption) of the target vapours from the preconcentrator must be kept very short.

Adsorbers of vapours are well known in the art of trace vapour analyzers, and are commonly employed for the purposes of preconcentration of selected vapours. Examples of such prior art adsorbers are disclosed in References 1-8 listed in Appendix A to this disclosure.

All such adsorbers rely on the absorption of the target vapours in a substantial volume of the adsorbent material. This creates a problem in respect of the speed of desorption of the vapours, because of the appreciable thermal mass of the adsorber material. A large thermal mass requires an appropriately large infusion of heat to raise it to the proper temperature of desorption. This also means that the adsorber will require a relatively long time to cool down to an effective adsorption temperature after desorption, thus creating unproductive time delays between successive measurements.

SUMMARY OF THE INVENTION

It is an object of an aspect of this invention to provide a novel preconcentrator which utilizes an adsorber material which is characterized by a high collection efficiency and a high degree of specificity for certain target organic vapours, and by the ability to release these target vapours in a very short period of time. It is a further object of an aspect of this invention that the above mentioned adsorber material also have the ability to decompose the target organic vapours, to release a decomposition vapour or vapours which are common to a family of target vapours, and thereby facilitate the detection of the entire family through the detection of the common decomposition vapour or vapours.

As discussed above, prior art adsorber material suffers from a problem in respect of the speed of desorption of the vapours, because of the appreciable thermal mass of the adsorber material. To overcome this problem, I have investigated the possibility of finding a material which is an effective and relatively specific adsorber of target organic vapours, which can be created in the form of a thin film on a suitable substrate, and yet is physically and chemically stable up to the temperature required for desorption of the target organic vapours. With these characteristics, a preconcentrator can then be made with the desired attributes mentioned above.

I have discovered that the desired adsorber material is found in the form of fullerenes. The term "fullerenes" is the name given to cage-like molecules of carbon in crystalline form. They constitute a new class of materials with radically different physical and chemical properties relative to earlier known forms of carbon, namely graphite and diamond. Although the active ingredients which are involved in the trapping of explosive molecules have not been fully characterized, it is known that these ingredients include $C_{60}$ and $C_{70}$ and larger fullerene molecules.

Fullerenes may be formed by high temperature vaporization of carbon and subsequent condensation of the carbon plasma, or by the combustion of alkylaromatic solvents and benzene. The most common fullerene constituents thus formed are $C_{60}$ and $C_{70}$. Higher mass components ($C_{74}$, $C_{76}$, $C_{78}$, $C_{82}$ and $C_{84}$ up to $C_{180}$) are also present, particularly in higher temperature combustion. A recent publication by the American Chemical Society (ACS Symposium No. 481—Fullerenes: Synthesis, Properties, and Chemistry of Large Carbon Clusters, George S. Hammond and Valerie J. Kuck, Editors, 1992) provides a good summary of the current state of knowledge on fullerenes.

I have discovered certain novel characteristics of fullerenes, which make them very useful in the detection of trace amounts of organic vapours in a sample of air, in particular for vapours arising naturally from nitroaromatics and those created by thermal evaporation of alkylnitrates, as discussed in greater detail below.

BRIEF DESCRIPTION OF THE DRAWINGS

A detailed description of the invention is provided herein below with reference to the following drawings, in which.

DETAILED DESCRIPTION OF THE PREFERRED EMBODIMENT

Figure 1:
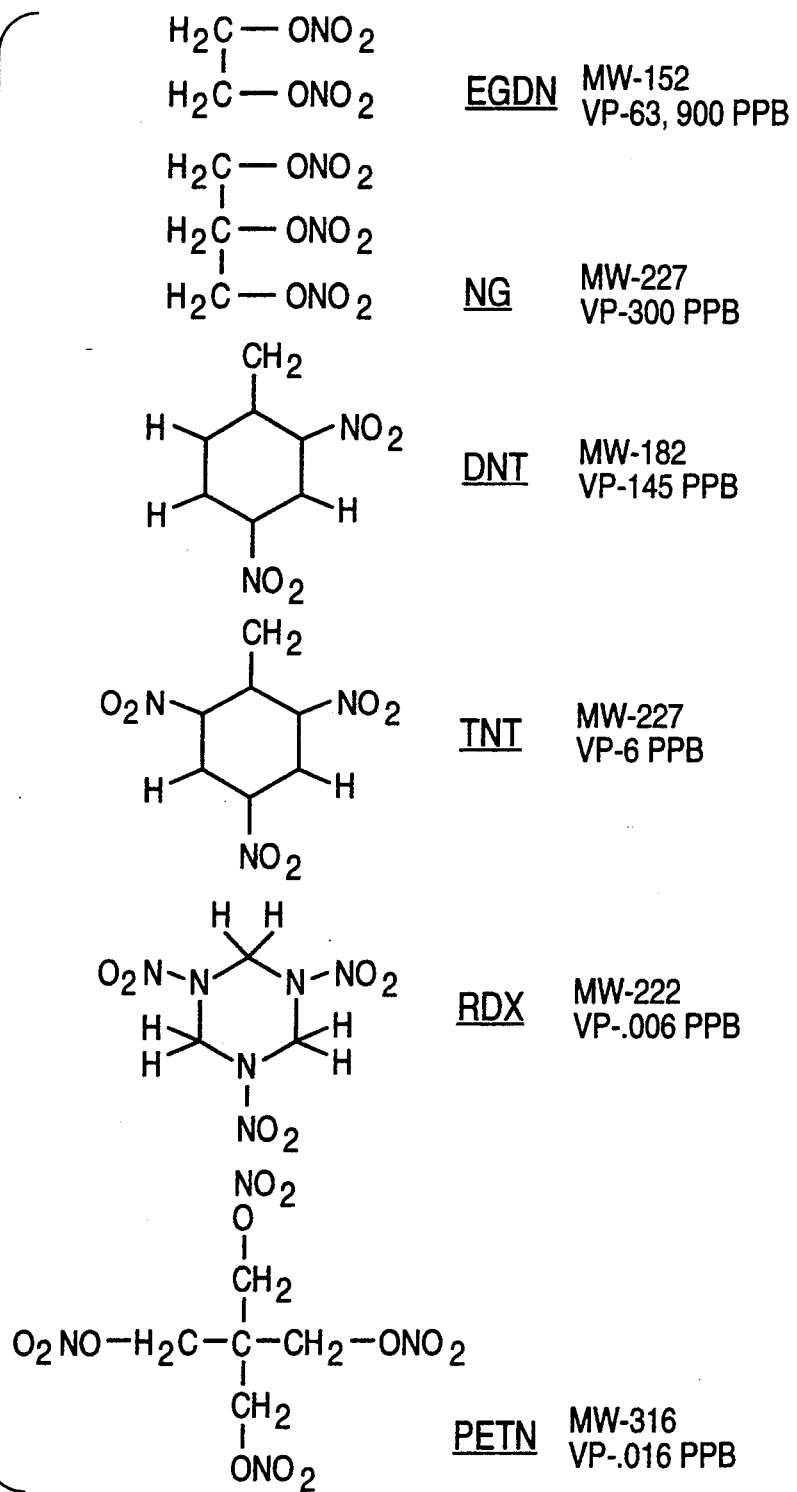
FIG. 1 illustrates the molecular structures and vapour pressures for selected explosives.

Returning to the discussion of fullerenes begun above in my Summary of Invention, it is known that fullerenes are soluble in benzene or toluene and chlorinated aromatics, and that such fullerenes can readily be deposited as thin films on clean metal surfaces, (e.g. nichrome wire). Once deposited, and thermally treated, the fullerenes adhere tenaciously to the metal surface and are difficult to remove. They are chemically and physically stable, up to temperatures on the order of 600° C. I have found that such thin films of fullerenes act as excellent adsorbers and collectors of organic vapours, in particular those of nitroaromatics or alkylnitrates (i.e. common explosives), such as illustrated in FIG. 1.

Because of their low thermal mass, the thin fullerene films can be rapidly heated, by resistive electrical heating of their substrate, to quickly desorb the organic vapours on their surface. This is an important advantage over prior art adsorber materials with respect to their application to explosive vapour detection, where time of measurement is often a critical factor.

An additional characteristic of thin fullerene films is that they act in a catalytic fashion, to promote the decomposition of the adsorbed vapours at temperatures which are lower than would otherwise have been required. For the purposes of the present invention, this is a very useful characteristic for the development of a portable explosive detector having low operating power requirements.

Most nitroaromatics and alkylnitrate based explosives undergo decomposition during heating and release $NO_2$, NO and other pyrolysis products (See References 9-11). The pyrolytic release of NO and $NO_2$ from explosive molecules is described by the following reaction, referred to herein as Reaction 1:

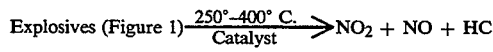

(1)

where HC is the hydrocarbon fragment of the molecule.

The ratio of $NO_2$ to NO is dependent on the temperature and the availability of oxygen for the oxidation of NO to $NO_2$. The $NO_2/NO$ ratio is also dependent on the type of explosive being pyrolyzed. Alkylnitrate, such as EGDN and PETN produce more $NO_2$ fragments, whereas, nitro-toluene explosives produce more NO fragment.

Similarly, all nitrogen containing compounds, such as cocaine and heroin can be pyrolyzed in the presence of oxygen (air) to produce molar amounts of NO and $NO_2$ (see Reaction 2, below), which are thus, detected with the electrochemical sensor.

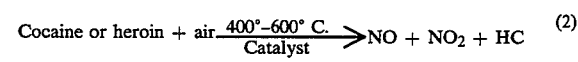

(2)

where HC is the hydrocarbon fraction, comprising $CO_2$ and $H_2O$.

EXAMPLE I—ADSORPTION OF EXPLOSIVES

Figure 2:
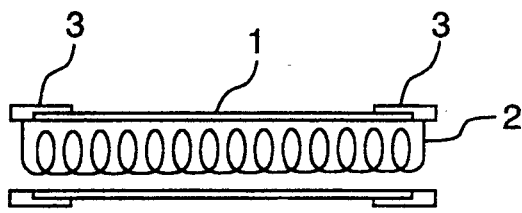
FIG. 2 is a schematic representation of a fullerenes coated wire tube for use in a preconcentrator according to the present invention.

The adsorption/desorption characteristics of fullerenes coated "wire tubes" will now be discussed with reference to FIG. 2. A collector/adsorber is shown in the form of a "wire tube" comprising a glass tube 1 containing a densely packed double helical coil of fine metal wire 2, which serves as a substrate. The ends of the wire coil 2 are fixed to two metal end caps 3 of the tube, thus permitting electrical contact for electrical heating of the wire. A vapour generator, described in Reference 12 was used to generate a known concentration of EGDN in the parts-per-trillion levels. Coated and uncoated tubes were used for sampling the vapour source for a fixed sampling time of 15 seconds. The sampler used in all tests, consisted of a diaphragm pump and an electrical timer for fixing the sampling at 15 seconds. Each sample tube was placed in turn in the sampler, and analyzed on an Explosive Vapour Detector, model EVD-8000.

The concentration of the vapour generator was ascertained by liquid injection of standard amounts of EGDN on a Tenax GC sample tube and from vapour sampling with the same tube and analysis in a model EVD-1 detector. The model EVD-1 detector is a portable gas chromatograph, equipped with a sensitive electron-capture detector (See Reference 13). Similarly, the model EVD-8000 detector is a portable GC/ECD system, but having the capability of rapid thermal desorption of the wire tube.

Samples of $C_{60}$ and $C_{70}$ were obtained from Aldrich Chemicals and used without further purification. These samples were dissolved in toluene, and solutions of 0.1 mg/cc were used for coating the wire tubes. Coating was effected by dipping the wire coils 2 into the solution and subsequent solvent evaporation by air drying at 70° C.

Sooting of the wire tubes was carried out by aspiration of toluene soot through the wire tube, followed by rinsing with acetone and air drying at 70° C. This left a residue of multiple fullerenes, as a thin film, on the wire coils 2.

Sampling results of 500 ppt (V/V) of EGDN from the vapour generator are shown below in Table 1 for uncoated, sooted tubes, and $C_{60}$ and $C_{70}$ wire tubes.

TABLE 1

| RUN # | UNCOATED TUBE | SOOTED TUBE 1 | SOOTED TUBE 2 | SOOTED TUBE 3 | C60 | C70 |
|---|---|---|---|---|---|---|
| 1 | 0 | 203 | 211 | 208 | 90 | 60 |
| 2 | 0 | 247 | 312 | 305 | 110 | 70 |
| 3 | 0 | 255 | 289 | 257 | 103 | 65 |
| 4 | 0 | 234 | 269 | 289 | 111 | 81 |
| 5 (AVE.) | 0 | 235 | 270 | 265 | 104 | 69 |

TABLE 1-continued

| RUN # | UNCOATED TUBE | TABLE I SOOTED TUBE 1 | SOOTED TUBE 2 | SOOTED TUBE 3 | C60 | C70 |
|---|---|---|---|---|---|---|
| (S.D) | | (23) | (43) | (43) | (10) | (9) |
| AMOUNT EGDN COLLEDTED.pg | | 59 | 68 | 66 | 26 | 17 |

Vapour source concentration = 500 ppt (v/v) of EGDN at 22 deg. C. and 760 mm Hg.

At low EGDN vapour concentration, the uncoated tube showed no vapour adsorption of EGDN at room temperature, whereas the fullerenes coated surfaces clearly showed adsorption of EGDN vapours. The $C_{60}$ and $C_{70}$ coated tubes showed lower efficiency of trapping EGDN in comparison with the sooted tubes, indicating that other active ingredients, presumably higher mass fullerenes, are responsible for part of the observed adsorption effect occurring on the coated wire/glass substrates, (i.e. the adsorption action of the various fullerenes is additive). It is, therefore, contemplated that this invention may be effected using higher order fullerenes as well, up to $C_{180}$.

The trapping efficiency of the soot coating on the nichrome wire is shown below in Table II. The collection efficiency of EGDN on the wire tube was determined by placing a Tenax packed tube in series with (i.e. after) the coated wire tube and analyzing the collected fraction on the Tenax tube. Repeated measurements showed that the average efficiency of the coated wire tube is about 47% of that of the Tenax tube (known to be 100% efficient), with a standard deviation of only 8%. The wire tubes analyzed on the EVD-8000 detector confirmed the efficiency to be in the range of 40%–51%.

TABLE II

| RUN # | TENAX GC TUBE IN SERIES WITH WIRE TUBE | TENAX GC TUBE ONLY | % COLLECTION EFFICIENCY |
|---|---|---|---|
| 1 | 501 COUNTS | 1123 COUNTS | 48 |
| 2 | 530 | 1129 | 53 |
| 3 | 610 | 1101 | 45 |
| 4 | 561 | 1131 | 50 |
| 5 | 660 | 1126 | 41 |
| 6 | 661 | 1131 | 42 |
| 7 | 580 | 1113 | 48 |
| AVE.(SD) | 586(62) | 1122(11) | 47(4) |

VAPOUR GENERATOR SET AT 250 PPT (V/V) OF EGDN. ALL ANALYSIS DONE ON THE EVD-1 (G.C/ECD DETECTORS) CORRECTIONS MADE FOR DIFFERENCES IN SAMPLING FLOWRATE WITH THE TENAX TUBE IN SERIES WITH THE WIRE TUBE

The efficiency of collection for other volatile explosives, such as nitroglycerine, 2,4 dinitrotoluene and the mononitrotoluene isomers was found to be in the range of 39–49%. Other non-volatile explosives, such as TNT, PETN and RDX (FIG. 1) were sampled by particulate collection or from swabbing techniques. Thermal desorption of the swab vapourized these explosives and allowed collection by condensation on the fullerenes coated wire tube. Considering the very small mass of the fullerenes film relative to the Tenax in the comparative collector, one can conclude that the fullerene films are remarkably efficient adsorbers of organic vapours arising from explosives.

As has been explained above, the significance of the small mass of the collector material is that it permits a very rapid desorption of the adsorbed vapours, with a low energy burden.

EXAMPLE II—EFFECT ON EXPLOSIVE DECOMPOSITION

Fullerenes from toluene soot were deposited on a quartz glass tube by suction through a toluene flame. The tube was rinsed with acetone and air dried at 70° C. A second quartz tube was similarly prepared, but uncoated.

The coated tube was placed in a SGE pyrojector, equipped with a temperature controller up to 900° C. The product of decomposition ($NO_2$) was monitored with a LMA-3, $NO_2$ chemiluminescence detector. The LMA-3 has a detection limit down to 10 pptv of $NO_2$.

Known amounts of EGDN from a standard solution were directly injected in the heated quartz tube. The $NO_2$ signal was measured on an external strip chart recorder. The pyrolyzer temperature was varied from 200° to 450° C. for the coated and uncoated quartz tubes.

Figure 3:
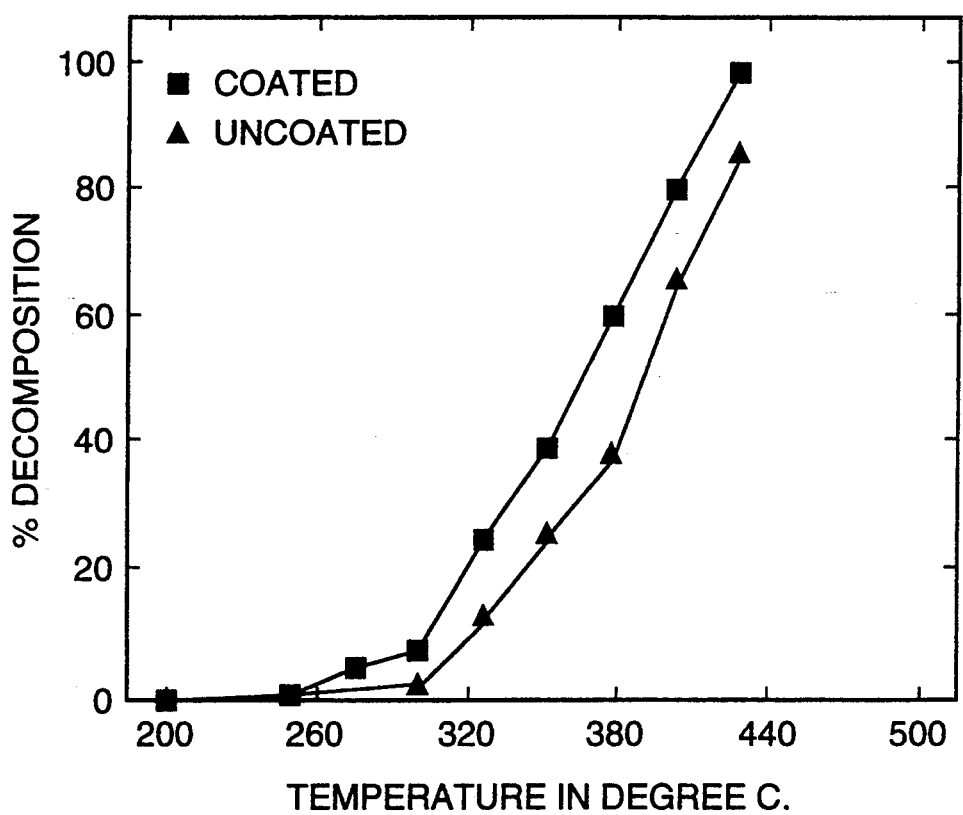
FIG. 3 is a graph showing pyrolysis of EGDN from coated and uncoated sooted surfaces for the wire tube of FIG. 2.

The percentage decomposition of EGDN as a function of pyrolyzer temperature is shown in FIG. 3. The coated tube shows some enhanced decomposition at lower temperatures in comparison to the uncoated quartz tube. This effect, although not shown here, is considerably more pronounced in plastic explosives, such as PETN and RDX (FIG. 1).

Figure 4:
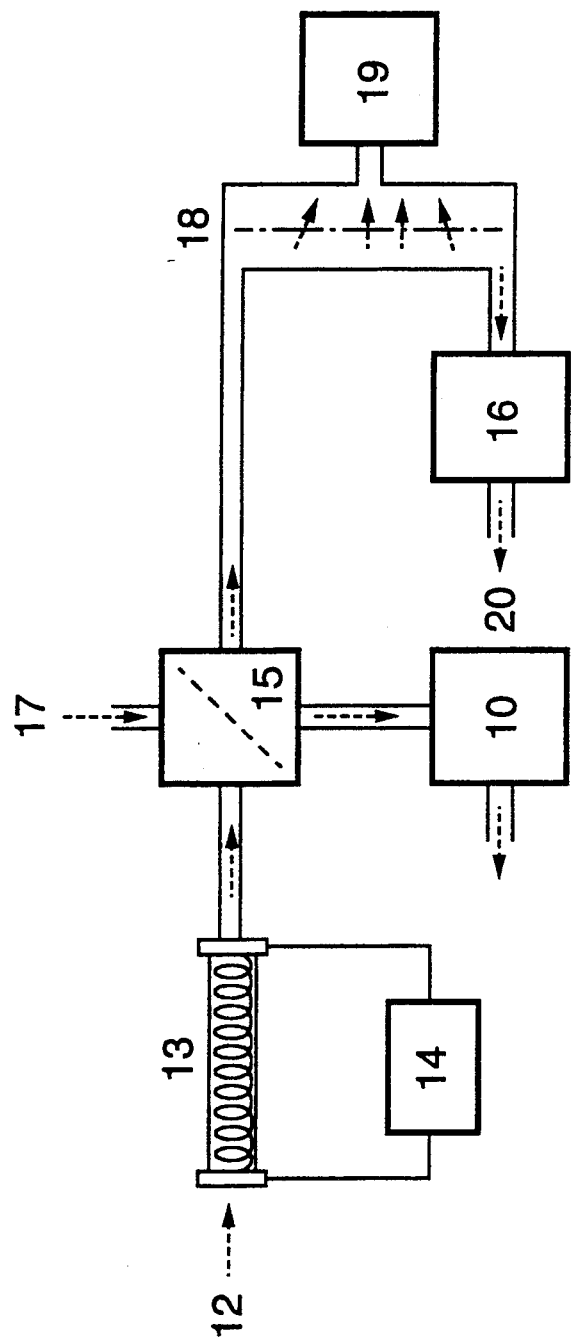
FIG. 4 is a schematic representation of a preconcentrator and detector according to the preferred embodiment of the present invention.

One specific embodiment of this invention is illustrated by FIG. 4. A sample pump 10 draws a sample of air 12 containing organic vapours to be detected, through a preconcentrator-adsorber 13 which consists of a metal substrate, coated with a thin film of fullerenes. A power supply 14 causes current to pass through the substrate, quickly heating it to a temperature which is optimum for the desorption and decomposition of the organic vapours which have been adsorbed on the concentrator. A teflon valve 15 then switches over so that a second pump 16 draws in carrier gas 17 and with it the desorbed and decomposed vapours. This combined gas then passes by a membrane 18 which selectively allows one or more of the desired vapours to pass to a detector 19. The rejected vapours and carrier gas are then vented 20.

The specific decomposition products of interest in respect of organonitrates are $NO_2$ and NO, either separately or in combination (see Reaction 1).

The specific decomposition products of interest in respect of illicit drugs are also NO and $NO_2$ either separately or in combination (see Reaction 2).

The detector 19 should be selected so as to be as sensitive and specific as possible for the detection of the desired decomposition product vapour or vapours. For example, for NO and $NO_2$, the detector may be an electrochemical or chemiluminescent-based sensor. For parent drug molecules, (i.e. not decomposed) the detector may be a surface ionization detector.

Of course, it is not necessary that the target organic vapours be decomposed on desorption, providing that the membrane 18 and detector 19 are selected so as to each be reasonably specific to the target vapours. For example, for organonitrates, the detector 19 may be an electron capture detector.

Other embodiments and modifications of the invention are possible. For example, the metallic substrate may be in the form of a flat ribbon rather than a helical coil 2, as shown in FIG. 2. All such embodiments and modifications are believed to be within the sphere and scope of the claims appended hereto.

APPENDIX A

Rerences (1) T. A. Griffy, Proceedings of the Third Symposium of Analysis and Detection of Explosives, Mannheim, Germany, 1989.
(2) D. P. Lucero, J. Test and Eval. 13,222, 1978.
(3) D. P. Lucero, Anal. Chemistry 40,707, 1968.
(4) J. R. Hobbs and E. Conde, Proceedings of the Third Symposium on Analysis and Detection of Explosives, Mannheim, Germany, 1989.
(5) K. Anderssen, J. Levin, C. Nilsson Chemosphere, 1983, 12 (6), pp. 821.
(6) S. Nacson, O. Legrady, T. Siu, and S. Nargolwalla, Proc. First Int. Symp. Explosive Detection Technology, FAA Atlantic City, N.J. Nov. 13-15, 1991, pp. 714-722.
(7) S. Nacson, C. Castledine, T. Siu, T. Lu and O. Legrady. Canadian Conference on Electrical and Computer Engineering, Ottawa, Ontario, Canada, Sep. 3-6, 1990.
(8) G. P. Cobb, R. S. Braman, Proceedings of the 1986 EPA/APCA Symp. on Measurement of Toxic Air Pollutants, pp. 314-319.
(9) T. Urbanski "Chemistry and Technology of Explosives" Pergamon Press: New York, 1965, Vol. 2, Chapter 6.
(10) A. L. Lafleur and K. M. Mills, Anal. Chemistry, 1981, 53 p.1202.
(11) J. Yinon, S. Zitrin "The Analysis of Explosives" Pergamon Press: New York, 1981.
(12) M. Krzymien and L. Elias, J. Phys. E.: Scientific Inst. Vol. 9, pp. 584-86, 1976.
(13) Explosives Detector Evaluation Report, FBI Laboratory, Forensic Science Research and Training Center, FBI Academy Quantico, Va. 22135, Mar. 21-24, 1988, pp.27-29.

I claim:

1. A system for detecting trace amounts of organic vapours in a sample of air, comprising:
  a) a preconcentrator-desorber for preconcentrating and desorbing said trace amounts of organic vapours from said sample of air, said preconcentrator-desorber including a metallic substrate, a film of fullerenes deposited on said metallic substrate for adsorbing said organic vapours on said film of fullerenes, thereby preconcentrating said organic vapours, and means for heating said metallic substrate to a predetermined temperature for desorbing said vapours from said film of fullerenes to form desorbed organic vapours for subsequent detection;
  c) a first pump and a second pump, each for drawing air into said system;
  d) a source of carrier gas;
  e) a valve having a first input connected to said preconcentrator-desorber, a second input connected to said source of carrier gas, a first output connected to said first pump and a second output connected to said second pump, for selectively (i) directing said sample of air through said preconcentrator-desorber to form said preconcentrated and then desorbed organic vapours, and (ii) directing a combination of said carrier gas and said desorbed organic vapours along a path of flow created by said second pump; and
  f) a detector in said path of flow created by said second pump for detecting said trace amounts of said organic vapours contained in said combination of said carrier gas and said desorbed organic vapours.

2. The apparatus of claim 1, wherein said predetermined optimum temperature is selected so as to both desorb and decompose said organic vapours to produce decomposition product vapours, and wherein said detector effects said detecting of said trace amounts of said organic vapours by detecting one or more of said decomposition product vapours for providing an indication of the presence of said organic vapours.

3. The system of claim 2, wherein said predetermined temperature is in the range of 300°-400° C. for detecting one or both of $NO_2$ and NO as said decomposition product vapours.

4. The system of claim 3, wherein said detector is a chemiluminescent detector for detecting one or both of $NO_2$ and NO.

5. The system of claim 3, wherein said detector is a electrochemical detector for detecting one or both of $NO_2$ and NO.

6. The system of claim 1 further comprising a membrane connected to said detector, said membrane being selectively permeable to one of either said organic vapours or a specific decomposition product vapour or vapours of said organic vapours to be detected, for enhancing the specificity of the detector.

7. The system of claim 1, wherein said fullerenes are selected from the group consisting of $C_{60}$ to $C_{180}$ inclusive.

8. The system of claim 1, wherein said organic vapours include those of alkylnitrates and nitroaromatics.

9. The system of claim 1, wherein said organic vapours include vapours arising from thermal vaporization of particulates, including alkylnitrates and narcotics.

10. The system of claim 1, wherein said metallic substrate is a nickel-chrome alloy.

11. The system of claim 1, wherein said metallic substrate is in the form of a double helical coiled wire.

12. The system of claim 1, wherein said metallic substrate is in the form of a flat ribbon.

* * * * *